US010463067B2

(12) United States Patent
Rosenberg et al.

(10) Patent No.: US 10,463,067 B2
(45) Date of Patent: *Nov. 5, 2019

(54) ORAL REHYDRATION COMPOSITION AND METHODS THEREOF

(71) Applicant: KALMARNA LIMITED, Road Town, Tortola (VG)

(72) Inventors: Alon Rosenberg, Rehovot (IL); Abraham Milstein, Rehovot (IL); Anthony Mackle, Co. Tyrone (GB); Ava Marie Firth, West Bridgford (GB); Monique Michele Schwartz, Keller, TX (US); Simon Van Dalsem, Alkmaar (NL); Arie Halpern, Pully (CH)

(73) Assignee: Kalmarna Limited, Tortola (VG)

( * ) Notice: Subject to any disclaimer, the term of this patent is extended or adjusted under 35 U.S.C. 154(b) by 24 days.

This patent is subject to a terminal disclaimer.

(21) Appl. No.: 15/527,724

(22) PCT Filed: Nov. 11, 2015

(86) PCT No.: PCT/IB2015/058699
§ 371 (c)(1),
(2) Date: May 18, 2017

(87) PCT Pub. No.: WO2016/079640
PCT Pub. Date: May 26, 2016

(65) Prior Publication Data
US 2017/0339997 A1 Nov. 30, 2017

Related U.S. Application Data

(60) Provisional application No. 62/081,588, filed on Nov. 19, 2014.

(51) Int. Cl.
*A23L 33/175* (2016.01)

(52) U.S. Cl.
CPC ......... *A23L 33/175* (2016.08); *A23V 2002/00* (2013.01); *A23V 2200/32* (2013.01); *A23V 2250/0618* (2013.01); *A23V 2250/0622* (2013.01); *A23V 2250/16* (2013.01); *A23V 2250/1614* (2013.01); *A23V 2250/5086* (2013.01); *A23V 2250/5482* (2013.01)

(58) Field of Classification Search
CPC .............. A23L 33/175; A23V 2002/00; A23V 2250/5482; A23V 2250/5086; A23V 2250/16; A23V 2250/0622; A23V 2250/0618; A23V 2200/32; A23V 2250/032; A23V 2250/1614; A23V 2250/262; A23V 2250/55
See application file for complete search history.

(56) References Cited

U.S. PATENT DOCUMENTS

| 4,652,454 A * | 3/1987 | Remesy ................ A23C 11/04 426/583 |
| 5,489,440 A | 2/1996 | Ndife et al. |
| 2003/0077333 A1* | 4/2003 | Phillips .............. A61K 31/7004 424/643 |
| 2007/0059362 A1* | 3/2007 | Rau ......................... A23L 2/395 424/466 |

FOREIGN PATENT DOCUMENTS

| CA | 2137469 A1 | 12/1993 |
| WO | 1997/042943 A1 | 11/1997 |
| WO | 2016/079640 A1 | 5/2016 |

OTHER PUBLICATIONS

Rubin S.I. et al., "Overview of Digestive System", Merck Veterinary Manual, retrieved from Internet on May 17, 2017, at: http://www.merckvetmanual.com/digestive-system/digestive-system-introduction/overview-of-digestive-system.
Voth D.E. et al, "Clostridium difficile Toxins: Mechanism of Action and Role in Disease", Clinical Microbiology Reviews, vol. 18, No. 2, Apr. 2005, pp. 247-263, American Society for Microbiology.
Mead S., "A Novel Prion Disease Associated with Diarrhea and Autonomic Neuropathy", The New England Journal of Medicine, vol. 369, Issue 20, Nov. 14, 2013, pp. 1904-1914.
"Diarrhoea or Scour", The Pig Site Pig Health, retrieved from Internet on May 17, 2017, at: http://www.thepigsite.com/pighealth/article/276/diarrhoea-or-scour/.
Constable P.D., "Antimicrobial use in the treatment of calf diarrhea", Journal of Veterinary Internal Medicine, vol. 18, Issue 1, Jan.-Feb. 2004, pp. 8-17.
Todar K., "Vibrio cholerae and Asiatic Cholera (p. 3)—Cholera Toxin", retrieved from Internet on May 17, 2017, at: http://www.textbookofbacteriology.net/cholera_3.html.
"What is the treatment for cholera?", Centers for Disease Control and Prevention, retrieved from Internet on May 17, 2017, at: https://www.cdc.gov/cholera/general/.
Mahalanabis D., et al, "Oral Fluid Therapy of Cholera Among Bangladesh Refugees", The Johns Hopkins Medical Journal, Bulletin of the World Health Organization, vol. 79, Issue 5, 2001, pp. 197-205.

(Continued)

*Primary Examiner* — Doan T Phan
(74) *Attorney, Agent, or Firm* — Akerman LLP

(57) ABSTRACT

An oral rehydration composition comprising the following: 1-glutamic acid in a range of about 0.01% to about 0.40% w/w and monosodium glutamate in a range of about 0.05% to about 0.80% w/w; about 1.50% w/w glucose monohydrate; about 0.20% w/w sodium chloride; about 0.15% w/w potassium chloride; about 0.35% w/w glycine; about 0.30% w/w trisodiumcitrate; about 0.15% w/w sodium dihydrogen phosphate; about 0.10% w/w xanthan gum; 85% Steviol Glycoside extract in a range of about 0.01% to about 0.03% w/w; about 0.20% w/w citric acid monohydrate; hydrolyzed whey in a range of about 0.15% to about 1.00% w/w; about 1.00% w/w hydrolyzed wheat; comprises cereals as a protein source; comprises enzyme co-factors; comprises a monosaccharide. The oral rehydration composition can be used on humans or animals that suffer from diarrhea.

14 Claims, No Drawings

(56) References Cited

OTHER PUBLICATIONS

"The International Pharmacopoeia—Sixth Edition, 2016", WHO Department of Essential Medicines and Health Products, retrieved from Internet on May 17, 2017, at: http://apps.who.int/phint/pdf/b/Jb.1.pdf.

Cesar G.V. et al., "Reducing deaths from diarrhoea through oral rehydration therapy", Bulletin of the World Health Organization, vol. 78, Issue 10, World Health Organization 2000, pp. 1246-1255.

"Clinical Management of Acute Diarrhoea", WHO/UNICEF joint statement, The United Nations Children's Fund/World Health Organization, May 2004.

Boron W. et al., "Medical Physiology", May 2016, Elsevier 2017, Chapters 41-46, pp. 852-971.

International Search Report of PCT/IB2015/058699, dated Jan. 26, 2016.

Written Opinion of the International Search Authority of PCT/IB2015/058699, dated Jan. 26, 2016.

International Preliminary Report on Patentability (Chapter II), of PCT/IB2015/058699, dated Feb. 7, 2017.

"Day 1 Enteral Nutrition For Critical Care + Oral Rehydration Support", Jorgen Kruuse A/S, Sep. 2014, retrieved from Internet on May 17, 2017, at: http://nozebra.ipapercms.dk/ViewFile30538.pdf.

Firth A. M. et al., "Oral rehydration therapy—simple administration of basic nutrients", The Veterinary Nurse, vol. 3 No. 7, Sep. 2012, pp. 438-443.

"Oral Rehydration Solution OS-1", retrieved from Internet on May 17, 2017, at: https://www.otsuka.co.jp/en/product/os1/.

Kelly D. G. et al., "Oral Rehydration Solution: A "Low-Tech" Oft Neglected Therapy", Nutrition Issues in Gastroenterology, Series No. 21, Practical Gastroenterology, Oct. 2004, pp. 51-62.

Alam A.N. et al., "Hydrolysed wheat based oral rehydration solution for acute diarrhoea", Archives of Disease in Childhood, vol. 62, 1987, pp. 440-444.

"Selected Summaries—Search for Super ORS", Indian Pediatrics, vol. 32, Sep. 1995, pp. 1047-1050, retrieved from Internet on May 17, 2017, at: http://www.indianpediatrics.net/sep1995/1047.pdf.

* cited by examiner

ORAL REHYDRATION COMPOSITION AND METHODS THEREOF

CROSS-REFERENCE TO RELATED APPLICATIONS

This application is a U.S. National Phase filing under 35 U.S.C. 371 of International (PCT) Patent Application No. PCT/IB2015/058699, filed 11 Nov. 2015, which claims priority from U.S. Patent Application No. 62/081,588, filed 19 Nov. 2014, both of which are incorporated by reference in their entirety.

BACKGROUND

This invention relates to oral rehydration products for the treatment of mammals suffering from gastrointestinal disorders which may arise from nutritional, parasitic, prional, bacterial, viral or protozoal causes and lead to fluid depletion, acidosis, and imbalances or loss of essential electrolytes. These diseases are causes clinical signs that are more severe in young animals and children, but may occur in adults of any species. Dehydration and electrolyte imbalances can cause death.

Normal Digestion

The functional goal of digestion is to break down complex foodstuffs into small component parts (nutrients) that can be absorbed by the intestine into the body, where said nutrients can be re-assembled into complex molecules that are necessary for the performance of normal body metabolism. The three major classes of foodstuffs are protein, carbohydrate and fat which are broken down into amino acids, sugars and lipids, respectively. Water and electrolytes (which are minerals such as sodium, potassium, chloride, and magnesium) are also required for maintenance of normal body metabolism. The ability of the gastrointestinal (GI) tract to digest food depends on a complex interaction of neuroendocrine responses that cause secretion of digestive enzymes and control the motility of the intestinal organs.

The first step in digestion is mechanical breakdown of the food, which is accomplished through chewing in the mouth, and then churning in the stomach. The stomach also serves as a reservoir in which digestive enzymes are mixed with the ingesta, causing the food to be broken down into a slurry. The slurry then passes from the stomach to the small intestine. The absorption of nutrients and electrolytes is almost entirely accomplished through the small intestine, whilst the large intestine is largely responsible for the resorption of water. The non-digestible residue of ingesta is excreted as feces.

In mammals with only one stomach, such as dogs, cats, pigs and humans, the digestive processes occur as described above. In herbivores (such as rabbits and horses) and ruminants (such as cattle and sheep), normal digestion also depends heavily on the activity of the microflora (bacteria, yeasts, and protozoa) of the rumen in ruminants, or of the cecum in horses and rabbits. The microflora in these species can digest cellulose; ferment carbohydrates to volatile fatty acids; and convert nitrogenous substances to ammonia, amino acids, and protein. In certain circumstances, the activity of the microflora can be suppressed to the point that digestion becomes abnormal or ceases. Incorrect diet, prolonged starvation or inappetence, and hyperacidity (as occurs in engorgement on grain) all impair microbial digestion. The microflora also may be adversely affected by the oral administration of drugs that are antimicrobial or that drastically alter the pH of rumen contents.

Gastroenteritis is a broad term that is used in both human and veterinary medicine to describe diseases of the GI tract that commonly result in vomiting and diarrhea, with severe impact upon digestion and absorption of nutrients. When used with precision, the term 'gastritis' refers to inflammation of the stomach, 'enteritis' refers to inflammation of the small intestine, and 'colitis' refers to inflammation of the large intestine. In actual practice, the afore-mentioned terms are often combined to reflect the broad impact of disease across the GI tract, resulting in terms such as gastroenteritis or enterocolitis. This document will subsequently use the term 'gastroenteritis' in its broadest sense as a collective noun referring to diseases and abnormalities of the gastrointestinal tract.

Causes of gastroenteritis are commonly divided into infectious and non-infectious causes. These are summarized in the table below.

| | Cattle, Sheep, and Goats | Pigs | Horses | Dogs and Cats | Humans |
|---|---|---|---|---|---|
| Viruses | Bovine viral diarrhea, rotavirus, coronavirus, rinderpest, malignant catarrhal fever, bluetongue, foot-and-mouth disease | Transmissible gastroenteritis, porcine circovirus type II, porcine epidemic diarrhea virus, rotavirus, foot-and-mouth disease, vesicular stomatitis, vesicular exanthema | Rotavirus, vesicular stomatitis, coronavirus | Canine parvovirus, canine coronavirus, feline panleukopenia virus, feline enteric coronavirus, canine and feline rotaviruses, canine and feline astroviruses | Norovirus, rotavirus |
| Rickettsiae | | | *Neorickettsia risticii* (Potomac horse fever [equine monocytic ehrlichiosis]) | *Neorickettsia helminthoeca* (salmon poisoning in dogs) | *R. rickettsii.* |

Common Causes of Gastroenteritis

| | Common Causes of Gastroenteritis | | | | |
|---|---|---|---|---|---|
| | Cattle, Sheep, and Goats | Pigs | Horses | Dogs and Cats | Humans |
| Bacteria | Enterotoxigenic Escherichia coli, Salmonella spp, Mycobacterium paratuberculosis, Fusobacterium necrophorum, Clostridium perfringens (types B, C, and D), Actinobacillus lignieresii, Yersinia enterocolitica, Campylobacter jejuni | Enterotoxigenic E coli, Salmonella spp, Brachyspira hyodysenteriae, Clostridium peifringens types B and C, Lawsonia intracellularis, Clostridium difficile | Enterotoxigenic E coli, Salmonella spp, Rhodococcus equi, Actinobacillus equuli, Clostridium perfringens types B and C, Clostridium difficile, Lawsonia intracellularis | Salmonella spp, Yersinia enterocolitica, Campylobacter jejuni, Bacillus piliformis, Clostridium spp, Mycobacterium spp, Shigella spp, adherent invasive E coli, Brachyspira spp | Salmonella, Campylobacter Staphylococci, Bacillus cereus, Clostridium perfringens, or Shigella spp; Escherichia coli; Clostridium difficile |
| Protozoa | Eimeria spp, Cryptosporidium spp | Eimeria spp, Isospora suis | Eimeria spp, Cryptosporidium spp | Isospora spp, Sarcocystis spp, Besnoitia spp, Hammondia spp, Toxoplasma spp, Giardia spp, Tritrichomonas spp, Entamoeba histolytica, Balantidium coli, Cryptosporidium spp, Neospora spp | Giardia sp, Entamoeba histolytica, Cryptosporidia spp |
| Yeast and Fungi | Candida spp (cattle) | Candida spp | Aspergillus fumigatus | Histoplasma capsulatum, Aspergillus spp, Candida albicans, phycomycetes | Candida spp |
| Algae | Prototheca spp | Prototheca spp | Prototheca spp | Prototheca spp | |
| Parasites (helminths) | Haemonchus, Ostertagia, Trichostrongylus Spp, Cooperia Spp, Bunostomum Sp, Strongyloides Sp, Nematodirus Spp, Toxocara Sp, Oesophagostomum Sp, Chabertia Sp, Trichuris Spp, Tapeworms | Ascaris sp, Macracanthorhynchus sp, Oesophagostomum spp, Strongyloides sp, Trichuris sp, | Gasterophilus spp, Habronema spp, Oxyuris sp, Parascaris sp, Large Strongyles, Small Strongyles, Strongyloides sp, Tapeworms, Trichostrongylus sp. | Spirocerca lupi, Physaloptera spp Ollulanus sp Strongyloides sp Roundworms Hookworms Whipworms Acanthocephalans Tapeworms Flukes | monogeneans, cestodes (tapeworms), nematodes (roundworms), and trematodes (flukes) |

Infectious Causes of Gastroenteritis

The GI tract is subject to infection by many pathogens, which are a major cause of economic loss due to illness, suboptimal performance, and death. As explained in the Merck Veterinary Manual, which is incorporated herein as a reference (http://www.merckmanuals.com/vet/digestive_system/digestive_system_introduction/overview_of_digestive_system.html, gastroenteritis may be caused by many different types of bacteria, viruses, and parasites.

Bacterial

Salmonellosis, enterotoxemia, and colibacillosis are examples of bacterial diseases of the GI tract. Many of the bacterial pathogens are part of the normal intestinal flora, and disease develops only after a stressful event, eg, salmonellosis in horses after transportation, or Clostridium difficile diarrhea after surgery in humans.

Clostridia are spore-forming bacteria that occur naturally in the soil and the intestinal tract of animals and humans. Diet change or stress may cause the normally inactive Clostridial bacteria in the intestines to become dominant, thus increasing in numbers and producing toxins. Different Clostridial species produce toxins which have various effects. For example, botulism and tetanus are both caused by Clostridial species. Clostridia *perfringens* produces an enterotoxin which destroys the tight junctions between the intestinal endothelial cells, resulting in severe diarrhea. Clostridia *difficile* is a notorious member of the Clostridia family and is the leading cause of hospital-acquired diarrhea in humans (Voth, D. E., & Ballard, J. D. (2005). *Clostridium difficile* toxins: mechanism of action and role in disease. *Clinical Microbiology Reviews*, 18(2), 247-63, which is incorporated herein as a reference).

Viral

Viral pathogens that cause disease of the GI tract are highly contagious. Important gastrointestinal viruses in veterinary medicine in include rotavirus, coronavirus, canine parvovirus, feline panleukopenia, bovine viral diarrhea (BVD), swine transmissible gastroenteritis (TGE) and porcine epidemic diarrhea virus (PEDv). Important viral pathogens in humans include noravirus and rotavirus.

Protozoal

Protozoa are one-celled parasites that infect the intestinal cells. Infections of small numbers of protozoa are common, and are often seen during microscopic fecal examinations in patients without evidence of disease. Patients infected with parasites are considered carriers and possible sources of infection for other susceptible animals or humans. The disease is caused by exposure and infections in young animals that have not been previously exposed. In veterinary medicine, common intestinal protozoal diseases include coccidiosis in young ruminants, dogs, cats, and poultry; trichomoniasis and giardiasis in dogs; and hexamitiasis in poultry. These diseases cause enteritis or colitis and are characterized by diarrhea, with or without blood and mucus. In humans, Giardia spp are the most common protozoa. Death from protozoal infection is related to dehydration and anemia. Diagnosis is based on the presence of clinical signs in the patient and detection of protozoa cysts or motile stages in the feces.

Parasitic

GI diseases caused by helminth (worm) parasites are not always clinically apparent, but both clinical and sub-clinical diseases affect the health of the patient. Nematodes (roundworms) are worms that commonly infect the GI tract of animals. Common species include trichostrongyles that infect the stomach and intestines of ruminants; strongyles which infect the large intestine of horses; hookworms which infect the small intestine of dogs and cats; large roundworms infecting the small intestine of pigs, dogs, cats, horses, and poultry; and whipworms infecting the large intestine of dogs and pigs. The parasitic larval stages of botflies (*Gasterophilus intestinalis*) infest and develop in the stomach of horses. In large numbers, bots may cause stomach pain and signs of colic in horses. Clinically affected horses display obvious signs of disease such as anemia, diarrhea, and emaciation.

The life span of worms is 1 to 12 months depending on the type of worm and level of resistance in the animal. Resistance affects how long the adult worms live and how many larvae survive as they enter an animal.

Large numbers of worms in the GI tract can affect the patient's health by causing a nutritional disturbance. Developing and migrating larvae and feeding adult worms can cause sufficient damage to the stomach lining and intestines. They also interfere with digestion and cause blood loss. Reduced enzyme secretion and nutrient absorption result in digestive inefficiency. Some worms suck blood and cause anemia and hemorrhage. Signs of disease are similar to the signs of malnutrition, including emaciation, changes in skin and hair, diarrhea, and anemia. Migratory larvae of roundworms can cause additional damage to the arteries, liver, and lungs of affected species.

Animals and people become infected when they swallow larvae (hairworms, strongyles, hookworms) or eggs (large roundworms, whipworms), when larvae penetrate the skin (hookworms), or when larvae enter the uterus or colostrum (hookworms, large roundworms).

Prions

Prions have classically been associated with neurological disease, namely transmissible spongiform encephalopathy in sheep, cattle and humans. However, a prion was recently reported to cause chronic diarrhea as well as autonomic nervous system abnormalities and peripheral neuropathy (Mead S, et al "A novel prion disease associated with diarrhea and autonomic neuropathy" *N Engl J Med* 2013; 369:1904-1914, which is incorporated herein as a reference).

Noninfectious Causes of Gastroenteritis

The major causes of noninfectious disease of the GI tract in all species include dietary overload or indigestible feeds, chemical or physical agents, obstruction of the stomach and intestines caused by the ingestion of foreign bodies or by any physical displacement or injury to the GI tract that interferes with the flow of ingesta, enzyme deficiencies, abnormalities of the mucosa that interfere with normal function (eg, gastric ulcers, inflammatory bowel disease, villous atrophy, neoplasms), and congenital defects. GI manifestations such as vomiting and diarrhea may also develop secondary to systemic or metabolic diseases such as uremia, liver disease, and hypoadrenocorticism.

Osmotic diarrhea is seen when inadequate absorption results in a collection of solutes in the gut lumen, which cause water to be retained by their osmotic activity. It develops in any condition that results in nutrient malabsorption or maldigestion or when an animal ingests a large amount of osmotically active substances that are not absorbed, eg, an overeating puppy or an excessively fatty meal in humans.

Malabsorption is failure of digestion and absorption due to some defect in the villous digestive and absorptive cells, which are mature cells that cover the villi. Intestinal malabsorption also may be caused by any defect that impairs absorptive capacity, such as diffuse inflammatory disorders (eg, lymphocytic-plasmacytic enteritis, eosinophilic enteritis) or neoplasia (eg, lymphosarcoma). Other examples of malabsorption include defects of pancreatic secretion that result in maldigestion. Rarely, because of failure to digest lactose (which, in large amounts, has a hyperosmotic effect), neonatal farm animals or pups may have diarrhea while they are being fed milk.

In noninfectious diseases of the GI tract, usually only a single animal is affected at one time. Exceptions are diseases associated with excessive feed intake or poisons, in which herd outbreaks are common.

Important Diseases Specifically Causing Diarrhea

Pigs: Diarrhea is the most common and probably the most important gastrointestinal disease of pigs, especially young piglets, as mentioned in "The Pig Site", which is incorporated herein as a reference (http://www.thepigsite.com/pighealth/article/276/diarrhoea-or-scour). In some outbreaks, diarrhea is responsible for high morbidity and mortality. In a well-run herd there should be less than 3% of litters at any one time requiring treatment and piglet mortality from diarrhea should be less than 0.5%. In severe outbreaks, levels of mortality can rise to 7% or more and in individual untreated litters up to 100% (in TGE it may reach 100% overall). Common causes of diarrhea in piglets are shown in the following table:

| THE MAIN CAUSES OF PIGLET DIARRHOEA | | | | |
|---|---|---|---|---|
| Early period days | | Late period days | | |
| 0-3 | 3-7 | 7-14 | 15-21 | Mortality level |
| Agalactia ✓ | ✓ | ✓ | ✓ | Moderate |
| Clostridia ✓ | ✓ | ✓ | | High |
| Coccidiosis | ✓ | ✓ | ✓ | Low |
| Colibacillosis ✓ (E. coli) | ✓ | ✓ | | Moderate |
| PED ✓ | ✓ | ✓ | ✓ | Low |
| PRRS ✓ | ✓ | ✓ | ✓ | Variable |
| Rotavirus | | ✓ | ✓ | Low |
| TGE ✓ | ✓ | ✓ | ✓ | High |

Four of the agents listed in the table are viruses, namely transmittable gastroenteritis (TGE), rotavirus, porcine epidemic diarrhea (PED) and porcine reproductive and respiratory syndrome (PRRS). The main bacterial causes are *Escherichia. coli* and Clostridia spp. The main parasite is coccidia.

Calves: Calf scours is the term used to describe gastroenteritis in calves. It is commonly incited by rotavirus or coronvirus infections, but other organisms such as *Cryptosporidium* (a protozoa) may also be causative. Regardless of the cause, calf scours is also complicated by bacterial overgrowth of *Escherichia coli* in approximately 30% of cases (Constable, P. D. (2004). Antimicrobial use in the treatment of calf diarrhea. *Journal of Veterinary Internal Medicine*, 18(1), 8-17, which is incorporated herein as a reference) Treatment consists of oral electrolyte solutions and, when appropriate, antimicrobials.

Puppies: Canine parvovirus is the most important cause of infectious diarrhea in young dogs. Parvovirus causes destruction of the intestinal cells, resulting in severe fluid loss and hemorrhagic diarrhea. If untreated, the mortality rate exceeds 80%.

Children: Cholera is an important cause of acute diarrhea in humans, and is caused by the bacteria *Vibrio cholerae*. Cholera is estimated to affect between 3 and 5 million people per year, and cause over 100,000 deaths. The *Vibrio cholerae* bacteria produces a toxin which causes the intestinal mucosal cells to secrete large quantities of chloride into the intestinal lumen, with subsequent loss of sodium, water and other electrolytes (http://www.textbookofbacteriology.net/cholera_3.html, which is incorporated herein as a reference) The treatment of choice is oral rehydration solution (http://www.cdc.gov/cholera/general/, which is incorporated herein as a reference).

Pathophysiology Mechanisms of Gastroenteritis

Both infectious and non-infectious causes of gastroenteritis result in a spectrum of disturbances in motility, intestinal distension, vomiting, diarrhea, fluid loss, hypersecretion and malabsorption.

Motility and Distension

Motility of the intestines depends on stimulation via the sympathetic and parasympathetic nervous systems (and thus on the activity of the central and peripheral parts of these systems) and on the GI musculature and its intrinsic nerve plexuses. Abnormal motor function usually manifests as decreased motility. Segmental resistance is usually reduced, and transit rate increases. One of the major consequences of subnormal motility is distention with fluid and gas. Much of the accumulated fluid is saliva and gastric and intestinal juices secreted during normal digestion. Distention causes pain and reflex spasm of adjoining gut segments. It also stimulates further secretion of fluid into the lumen of the gut, which exacerbates the condition. When the distention exceeds a critical point, the ability of the musculature of the intestinal wall to respond diminishes, the initial pain disappears, and paralytic ileus develops in which all GI muscle tone is lost. Dehydration, acid-base and electrolyte imbalance, and circulatory failure are major consequences of GI distention.

Vomiting is a neural reflex act that results in ejection of food and fluid from the stomach through the oral cavity. It is associated with antecedent events such as premonition, nausea, salivation, or shivering and is accompanied by repeated contractions of the abdominal muscles.

Diarrhea is caused by disruption of the normally continuous transfer of electrolytes and water across the intestinal mucosa. Normally, secretion (from bloodstream to intestinal lumen) and absorption (from intestinal lumen to bloodstream) occur simultaneously. In normal health, 99% of the fluid resulting from oral intake and GI tract secretions is reabsorbed by the small intestine and colon. In humans, this is a total fluid load of about 9 of 10 L daily. Thus, even a 1% change in this balance between resorption and secretion can result in significant fluid losses and diarrhea.

Three major pathophysiologic mechanisms result in diarrhea. These are increased permeability, hypersecretion, and villous destruction. Increased permeability caused by inflammation in the intestines can be accompanied by an increase in "pore size" in the intestinal mucosa, permitting increased flow through the membrane ("leak") down the pressure gradient from blood to the intestinal lumen. If the amount exuded exceeds the absorptive capacity of the intestines, diarrhea results. The size of the material that leaks through the mucosa varies, depending on the magnitude of the increase in pore size. Large increases in pore size permit exudation of plasma protein, resulting in protein-losing enteropathies (eg, lymphangiectasia in dogs, paratuberculosis in cattle, nematode infections). Greater increases in pore size result in the loss of red blood cells, producing hemorrhagic diarrhea (e.g., hemorrhagic gastroenteritis, parvovirus infection, severe hookworm infection).

Hypersecretion is a net intestinal loss of fluid and electrolytes. Hypersecretion can be due to enterotoxins, osmotic load, malabsorption or destruction of the intestinal villi. Enterotoxic colibacillosis is an example of diarrheal disease due to enterotoxins. Certain variants of the bacterial *Escherichia coli* produce enterotoxin that stimulates the crypt epithelium to secrete fluid beyond the absorptive capacity of the intestines. The fluid secreted is isotonic, alkaline, and free of exudates. The villi, along with their digestive and absorptive capabilities, remain intact. The fact that the villi remains intact is the basis of oral rehydration therapy in this particular disease, because a fluid administered orally that contains glucose, amino acids, and sodium is absorbed, even in the face of hypersecretion.

Transmissible viral diseases often cause destruction of the villi. Some epitheliotropic viruses directly infect and destroy the villous absorptive epithelial cells, e.g., coronavirus, transmissible gastroenteritis virus of piglets, and rotavirus of calves. Feline panleukopenia virus and canine parvovirus destroy the crypt cells, which results in failure of renewal of villous absorptive cells and collapse of the villi; thus regeneration is a longer process after parvoviral infection than after viral infections of villous tip epithelium (eg, coronavirus, rotavirus). Reduced secretion of digestive enzymes at the surface of villous tip cells is characteristic of epitheliotropic viral infections recognized in farm animals.

Clinical Findings of GI Disease

Signs of GI disease include excessive salivation, diarrhea, constipation or scant feces, vomiting, regurgitation, GI tract hemorrhage, abdominal pain and distention, tenesmus, shock and dehydration, weight loss and suboptimal performance. Vomiting is most common in single-stomached animals and humans. Horses, rabbits and ruminants do not vomit. Large-volume, fluid diarrhea usually is associated with hypersecretion (eg, in enterotoxigenic colibacillosis in newborn calves) or with malabsorptive (osmotic) effects. Blood and fibrinous casts in the feces indicate a hemorrhagic, fibrinonecrotic enteritis of the small or large intestine, eg, bovine viral diarrhea, coccidiosis, *salmonellosis*, or swine dysentery. Abdominal distention can result from accumulation of gas, fluid, or ingesta. Varying degrees of dehydration and acid-base and electrolyte imbalance, which may lead to shock and death, are seen when large quantities of fluid are lost through vomiting or diarrhea.

Treatment and Control of Gastroenteritis

Whenever possible, elimination of the cause of the disease or the source of the infection is the primary objective. Elimination of the primary cause may involve antimicrobials, coccidiostats, antifungal agents, anthelmintics, antidotes for poisons, or surgical correction of displacements. In epidemic situations such as swine dysentery and human cholera, massive disinfection and development of clean water sources may be required.

After the cause or source is eliminated, treatment is supportive and symptomatic, aimed at relieving pain, correcting fluid and electrolyte abnormalities, and providing such nutritional support as can be tolerated by the patient.

Replacement of fluid and electrolytes is necessary when dehydration and electrolyte and acid-base imbalance occur as in diarrhea, persistent vomiting, intestinal obstruction, or torsion of the stomach(s), in which large amounts of fluid and electrolytes are sequestered. An oral glucose-electrolyte solution can be given if diarrhea is not severe and nausea and vomiting are minimal. Severe diarrhea requires fluid and electrolyte replacement to correct dehydration, electrolyte imbalance, and acidosis. Oral and parenteral (intravenous) fluids are sometimes given simultaneously when water and electrolytes must be replaced in massive amounts. Intravenous fluids containing sodium chloride, potassium, glucose and bicarbonate precursor molecules such as lactate and acetate are often administered to individual patients, but their use is precluded in farm animal herd situations and in some human epidemic situations.

Correction of excessive or depressed motility appears rational, but often the nature and degree of abnormal motility are uncertain; in addition, available drugs may not give consistent results. There is little clinical evidence to recommend the routine use of anticholinergic or opioid drugs to slow intestinal transit. Slowing intestinal transit may be counterproductive to the defense mechanism of diarrhea, which acts to evacuate harmful organisms and their toxins. In general, anticholinergic drugs probably are justified only for short-term symptomatic relief of pain and tenesmus associated with inflammatory diseases of the colon and rectum. In some disorders of gastric or colonic motility, prokinetic drugs (eg, metoclopramide, erythromycin) may be useful.

Relief of distention medically by stomach tube (as in bloat in ruminants) or surgically (as in acute intestinal obstruction, or in torsion of the abomasum in ruminants or of the stomach in monogastric animals) may be required. The GI tract may become distended with gas, fluid, or ingesta at any level due to physical or functional obstruction.

Relief of abdominal pain by administration of analgesics should be done when the pain is reflexly affecting other body systems (eg, cardiovascular collapse) or when it is causing the animal to injure itself because of rolling, kicking, or throwing itself. Animals treated with analgesics must be monitored regularly to ensure that the relief of pain does not provide a false sense of security; the lesion may be progressively worsening while the animal is under the influence of the analgesic. Reconstitution of ruminal flora should be done in situations in which the ruminal flora may be seriously depleted (eg, in prolonged anorexia or acute indigestion). Transfaunation (ruminal fluid transfer) involves oral administration of ruminal contents from a healthy animal that contains rumen bacteria and protozoa and volatile fatty acids.

PRIOR ART

The principles of oral rehydration therapy are based upon supplying simple nutrients that can be absorbed directly by the cells lining the small intestine, known as enterocytes. Enterocytes are responsible for absorbing the final products of digestion that was accomplished by the stomach and enzymes released from the pancreas and small intestine. Digestion reduces the three main categories of nutrients—carbohydrates, proteins and fats—into their constituent molecules, namely sugars, amino acids and lipids.

The goal of digestion is to break ingested food into small molecules that can readily be absorbed by the enterocytes. However, enterocytes are not capable of absorbing anything larger than peptide chains of up to four amino acids, and preferably single amino acids (Textbook of Medical Physiology, Boron and Boulpaep, incorporated herein as a reference). These individual amino acids are transported into the blood stream and circulated to the rest of the body, where they are re-assembled into proteins. Similarly, only single sugar molecules (monosaccharides) such as glucose, fructose and galactose can be absorbed into the enterocyte and enter the blood stream, to be used for energy by the body's cells. The transport of amino acids and sugar molecules into the enterocyte is dependent upon specialized transporter molecules that are built into the enterocyte's cell wall. These transporter molecules require a certain concentration of sodium available to them in order to accomplish their task. In recognition of these physiologic limitations, oral rehydration therapy solutions generally contain very simple sugars (usually glucose), single amino acids or else peptides of only two or three amino acids. Most oral rehydration therapy solutions contain little or no fat, since high-fat diets are poorly tolerated in cases of vomiting and diarrhea. Oral rehydration therapy solutions are also usually isotonic, with an osmolarity of about 300 mOsm/L. This ensures that oral rehydration therapy solutions are readily absorbed without creating further sodium or water loss. Since electrolyte depletion is also a feature of acute diarrhea, most oral rehydration solutions also contain quantities of sodium and potassium as well as variable levels of other electrolytes.

Following the trends of human medicine, veterinary medicine has developed oral rehydration therapy products for use in both large and small animals. These are typically provided in powdered form and may contain anti-caking agents such as sodium citrate or citric acid which decrease palatability. These formulations need to be reconstituted by owners or veterinary staff and care must be taken to mix them correctly. Ideally, these formulations should be reconstituted with boiled water, but often un-boiled water is used. Furthermore, often tap water, which may contain chlorine or other impurities, is used. These practices can result in the reconstituted aqueous product possibly being contaminated or having altered, undesirable electrolyte properties. Some prior known veterinary oral rehydration therapy products contain sodium citrate or citric acid.

Previous (prior art) compositions for treatment of severe gastroenteritis and diarrhea have focused on oral administration of essential electrolytes, sugar and water. The original developer of this approach was the World Health Organization (WHO) (Mahalanabis, D., Choudhuri, A. B., Bagchi, N. G., Bhattacharya, A. K., & Simpson, T. W. (1973). Oral Fluid Therapy of Cholera among Bangladesh Refugees. The Johns Hopkins Medical Journal, 79(5), 473-479, which is incorporated herein as a reference), which introduced an oral, isotonic electrolyte solution for treatment of cholera in humans. This formula is also considered suitable for the treatment of gastroenteritis in many species and is used particularly in dogs and cats. (Saunders Comprehensive Veterinary Dictionary, which is incorporated herein as a reference).

The WHO formula for oral rehydration therapy is now widely accepted (Monographs: Dosage forms: Specific monographs: Sales perorales ad rehydratation—Oral rehydration salts—The International Pharmacopaeia, 4th supplement, 2014—http://apps.who.int/phint/en/p/docf/, which is incorporated herein as a reference) and comprises the following ingredients:

| sodium chloride | NaCl | 2.6 g |
| trisodium citrate dihydrate | C6H5Na3O7, 2H2O | 2.9 g |
| potassium chloride | KCl | 1.5 g |
| anhydrous glucose | C6H12O6 | 13.5 g |

In this formulation, glucose is the only carbohydrate and the only ingredient that is a metabolizable energy source.

Patent application WO1997042943A1 provides an oral rehydration composition comprising a composition to be made up in water at point of use as an oral rehydration formulation, which composition comprises glutamine which is effective to enhance nutritional uptake, and an appropriate mixture of a metabolizable energy source, electrolytes, bicarbonate precursors, and alkali metals, especially sodium, the concentration of sodium being about 120 millimoles per liter (mmol/l) of final formulation.

Patent application CA2137469A1 provides a composition for the treatment of livestock suffering from disorders such as fluid depletion, acidosis, and imbalances or loss of essential electrolytes, same to be made up in water at point of use as an oral rehydration formulation, comprises an intimate mixture of an energy source, electrolytes, and bicarbonate precursors, which precursors are provided as physiologically acceptable carboxylic acid anions with corresponding physiologically acceptable cations including sodium, the yield of bicarbonate being in excess of 30 millimole/liter (mmol/l) of final formulation, and the concentration of sodium being in excess of 80 mmol/l of final formulation.

U.S. Pat. No. 5,489,440A provides a method for producing an improved rice flour-based oral rehydration solution using the enzymes cellulase and protease. The oral rehydration solution of the invention has low viscosity, low osmolality, and can be ingested through the nipple of a bottle. The oral rehydration product can also be dried into powder form before packaging and reconstituted at the time of use. The product is designed to treat individuals with severe diarrhea brought about by cholera or other causes.

Although many versions of oral rehydration formulas have been patented, there is still a long felt need for a formula that will provide with a more extensive complete formula to treat humans and animals during the disease period. The novel formula must be based upon a more in-depth understanding of cellular physiology. Oral rehydration for the last forty years has focused upon the provision of simple salts, sugars and water, under the assumption that replacing these will lead to improved survival of targeted patients. Survival in humans has undoubtedly improved (Victora C G, Bryce J, Fontaine O, Monasch R (2000) Reducing deaths from diarrhoea through oral rehydration therapy. Bull World Health Organ 78: 1246-55, which is incorporated herein as a reference) but the recipe for oral rehydration has remained largely unchanged in this time (clinical management of acute diarrhea, WHO/FCH/CAH/04.7, which is incorporated herein as a reference).

Research has shown that the enterocytes actually require and use particular amino acids, rather than glucose, in order to maintain their own cellular function and integrity. The intent of this patent is to describe a method of providing, not only hydration for humans and animals, but also the energy substrate required by the enterocytes in order to preserve the enteral functionality.

SUMMARY

An oral rehydration composition comprising the following: l-glutamic acid in a range of about 0.01% to about 0.40% w/w and monosodium glutamate in a range of about 0.05% to about 0.80% w/w; about 1.50% w/w glucose monohydrate; about 0.20% w/w sodium chloride; about 0.15% w/w potassium chloride; about 0.35% w/w glycine; about 0.30% w/w trisodiumcitrate; about 0.15% w/w sodium dihydrogen phosphate; about 0.10% w/w xanthan gum; 85% Steviol Glycoside extract in a range of about 0.01% to about 0.03% w/w; about 0.20% w/w citric acid monohydrate; hydrolyzed whey in a range of about 0.15% to about 1.00% w/w; about 1.00% w/w hydrolyzed wheat; comprises cereals as a protein source; comprises enzyme co-factors; comprises a monosaccharide.

The oral rehydration composition is tailored to suit the flavouring preferences of different species or individuals.

The oral rehydration composition is a ready-to-use composition. Can be manufactured as a powder concentrate that is diluted in water. It can also be gel, spray, quick dissolve tablet and other preparations. The important feature is that it will be always a ready to use oral formulation.

The oral rehydration composition of any of the examples 1-5.

The oral rehydration composition can be a hypertonic, a hypotonic or an isotonic solution comparable to the isotonicity of a 0.9% solution of sodium chloride.

A method of preventing dehydration comprising the steps of: preparing an oral rehydration solution; administering said oral rehydration solution to the individual; wherein said composition comprises l-glutamic acid in a range of about 0.01% to about 0.40% w/w and monosodium glutamate in a range of about 0.05% to about 0.80% w/w.

The individual in the method is a human and/or an animal.
The individual in the method is suffering from diarrhea.

DESCRIPTION

This invention relates to oral rehydration products for the treatment of mammals suffering from gut disorders which may arise from nutritional, bacterial, prional, viral or protozoal causes and lead to fluid depletion, acidosis, and imbalances or loss of essential electrolytes. These problems typically arise in immature animals such as pigs, calves, lambs, foals, and puppies, but may in fact occur in patients of any age and species, including humans. Although this invention is primarily intended to be applied in the treatment of pigs, calves, lambs, foals or dogs with diarrhea, and description of the invention herein will be related thereto, it will, however, be appreciated that other animals, including humans, may also suffer from abnormal conditions leading to similar dehydration, acidosis and electrolyte loss for which these products may be used.

A primary feature of this invention is to support the metabolic processes and energy requirements of enterocytes and other intestinal cells. Enterocytes serve as the bridge between the lumen of the small intestine and the bloodstream that delivers nutrients to the rest of the body. However, enterocytes themselves require nutrients with which to accomplish their own processes, and research has shown that enterocytes may prefer certain amino acids as their fuel source, rather than monosaccharides The present invention seeks to provide an improved oral rehydration product.

The microenteral nutrition formula of this inventions is specifically designed to deliver small amounts of water, electrolytes and readily absorbed nutrients (glucose, amino acids, and small peptides) directly to the gastrointestinal tract. It is easy to digest and rapid to absorb.

The formula is designed to do two important roles for animals:

1. nourish the enterocyte cells lining the small intestine during periods of vomiting and diarrhea, these cells both create the mucus that provides the protective barrier of the intestine (preventing bad bacteria from entering the blood stream and affecting other parts of the body) and the enterocytes also are the absorptive cells that pull in nutrition needed by the body. Without direct nutrition (which often occurs during vomiting/diarrhea, when the animal is not eating) these cells die/atrophy quickly. Other formulas available tend to offer only electrolyte replacement to tackle the dehydration, or are complete diet/milk replacers delivering amino acids, but are too high in fat and protein for the gut to tolerate during periods of gastroenteritis.
2. Provide fast acting rehydration support, through a palatable isotonic formula, that will absorb quickly delivering the essential electrolytes and fluids the body needs for recovery and also with a palatable sweet/slightly acidic taste that will encourage animals to drink more fluids for longer. It is known that plain water is known to shut down the thirst mechanism early, reducing the fluid intake, adding flavor (sweetener or other) maintains the thirst mechanism encouraging the animal to consumer more fluids for longer.

Accordingly, it is an object of the present invention to provide a liquid rehydration formulation for oral administration comprising water, electrolytes, and a monosaccharide. The formulation may or may not include sodium citrate or citric acid. Ideally, the formulation includes a flavour enhancer for those species which find flavors palatable.

It is a further object of this invention to provide a liquid rehydration formulation for oral administration comprising water, electrolytes, a flavour enhancer for those species which find flavors palatable and a source of simple sugar. The formulation may or may not include sodium citrate or citric acid. Ideally, the formulation includes a protein source.

It is a further object of this invention to provide a liquid rehydration formulation for oral administration comprising water, electrolytes and a monosaccharide, with or without sodium citrate or citric acid being present. Preferably, the oral liquid rehydration formulation further includes a flavour enhancer and/or a protein source.

It is a further object of this invention to provide a liquid rehydration formulation for oral administration comprising water, electrolytes, a flavour enhancer and/or a protein source and a monosaccharide. The formulation may or may not include sodium citrate or citric acid. Ideally, the formulation includes the amino acid glutamate.

It is a further object of this invention to provide a liquid rehydration formulation for oral administration comprising water, electrolytes, a flavour enhancer and/or a protein source, a monosaccharide and the amino acid glutamate. The formulation may or may not include sodium citrate or citric acid. Ideally, the formulation includes any combination of amino acids containing glutamate.

It is a further object of this invention to provide a liquid rehydration formulation for oral administration comprising water, electrolytes, a flavour enhancer and/or a protein source, a monosaccharide and any combination of amino acids containing glutamate. The formulation may or may not include sodium citrate or citric acid. Ideally, the formulation includes enzyme co-factors such as zinc or magnesium.

It is a further object of this invention to provide a liquid rehydration formulation for oral administration, from a group comprising of: L-Glutamic Acid, and its salts as Glutamates, L-Glutamine, L-Arginine, carnitine, taurine, alpha-ketoglutarate and leucine and any combination thereof.

Further including in this invention vegetable and animal protein concentrates which are naturally rich in glutamic acid and glutamates, such as derived from wheat, whey, maize, rice, barley, soy, peanut, sunflower seed, and other grains and oilseeds.

For Animal Protein concentrates this can be Milk Protein, Whey Protein, Egg White Protein, Blood Plasma Protein and other animal protein sources.

Both the natural forms of vegetable and animal protein concentrates can be used, and preferably in their enzymatically or chemically hydrolysed form as this can make the absorption more efficient.

Accordingly, it is an object of the present invention to provide a liquid rehydration formulation for oral administration comprising water, electrolytes, and a monosaccharide. The formulation may or may not include sodium citrate or citric acid. Ideally, the formulation includes a hydrolyzed wheat or whey protein source.

It is a further object of this invention to provide a liquid rehydration formulation for oral administration comprising water, electrolytes, a hydrolyzed wheat or whey protein source and a source of simple sugar. The formulation may or may not include sodium citrate or citric acid. Ideally, the formulation includes a flavor enhancer. In a preferred arrangement, the enhancer is a sweetener such as Steviol Glycoside extract.

It is a further object of this invention to provide a liquid rehydration formulation for oral administration comprising water, electrolytes and a monosaccharide, with or without sodium citrate or citric acid being present. Preferably, the oral liquid rehydration formulation further includes a hydrolyzed wheat or whey protein source and a flavor enhancer.

It is a further object of this invention to provide a liquid rehydration formulation for oral administration comprising water, electrolytes, a hydrolyzed wheat or whey protein source, a flavor enhancer, and a monosaccharide. The formulation may or may not include sodium citrate or citric acid. Ideally, the formulation includes the amino acid glutamate.

It is a further object of this invention to provide a liquid rehydration formulation for oral administration comprising water, electrolytes, a hydrolyzed wheat or whey protein source, a flavor enhancer, a monosaccharide and the amino acid glutamate. The formulation may or may not include sodium citrate or citric acid. Ideally, the formulation includes any combination of amino acids containing glutamate.

It is a further object of this invention to provide a liquid rehydration formulation for oral administration comprising water, electrolytes, a flavor enhancer, a hydrolyzed wheat or whey protein source, a monosaccharide and any combination of amino acids containing glutamate. The formulation may or may not include sodium citrate or citric acid. Ideally, the formulation includes enzyme co-factors such as zinc or magnesium.

In a preferred aspect, the oral liquid rehydration formulation is an isotonic solution. Ideally, it is an isotonic, electrolyte balanced formulation. The electrolyte composition of the solution is ideally tailored to suit animals, such as pigs, calves, lambs, foals, chickens, puppies and humans, to which the formulation is intended to be administered in use.

In another preferred aspect, the oral liquid rehydration formulation is provided as a powder mix to be dissolved in water or added to the food.

In another preferred aspect, the oral liquid rehydration formulation is provided as a ready to use solution—which would preferably be manufactured in bulk containers, ready to be administered into drinking systems.

In another preferred aspect, the oral liquid rehydration formulation is provided as a liquid concentrate mix to be diluted in water.

The term "flavour enhancer" as used herein is meant to include any food-grade material which has a flavour which is palatable to animals, such as pigs, calves, lambs, foals, chickens, puppies and humans, to which the formulation is intended to be administered in use.

Different non-meat flavor enhancers and\or protein sources may be used, including wheat or whey extract, wheat or whey hydrolysates, hydrolysed whey protein and lyophilized wheat or whey.

In a most preferred arrangement, the protein source is pre-treated to reduce at least a portion of the protein present to single amino acids and or peptides of up to about 10 amino acids, preferably four amino acids or less.

For ill animals, it is critical to encourage them to take liquid, and the oral liquid rehydration formulation of the invention is designed to enhance fluid intake by supplying a liquid isotonic, electrolyte balanced drink which is palatable to the animal due to the inclusion of a flavoring which the animal likes. The flavor enhancer is ideally also a protein source and thus provides the ill animal with protein in an acceptable, palatable form.

As the protein source is intended to supply easily digestible and absorbable amino acids and peptides to a sickly animal receiving the oral liquid rehydration formulation of the invention, the protein source is ideally meat or meat extract selected to be flavorsome to an animal in need thereof so as to encourage the animal to consume the formulation. It is also desirable to select the protein source so that it complements the dietary needs of the animal receiving it. For example, chicken liver has been shown to be suitable for pigs since it is a rich source of essential and conditionally-essential amino acids which pigs need to be supplied in their diet.

Ideally, the sugar is a monosaccharide such as glucose, fructose, or galactose.

Since sodium citrate and citric acid have a flavor which dogs, in particular, dislike, it is ideal to omit this from the oral liquid rehydration formulation for the specific type of animals. Its function as a preservative is rendered unnecessary in the liquid formulation of the present invention since prior art oral rehydration products for veterinary use were supplied in powdered form and required to be reconstitution using water when needed. Such products, as mentioned above, always included sodium citrate or citric acid. It has now been found that sodium citrate and citric acid can be omitted without compromising beneficial properties of the formulation, and that omitting same actually has the advantage of rendering the formulation more palatable for these type of animals. Thereby, the usage of sodium citrate, citric acid and/or their salts in the present invention can be omitted where relevant. It is also important to emphasize that the mere exclusion of sodium citrate or citric acid, doesn't make the oral rehydration product palatable to dogs. It is important to find the right combination of ingredients for each type of animal.

Though the oral liquid rehydration formulation of the present invention contains biological-origin ingredients, it can be manufactured according to Hazard Analysis and Critical Control Point (HAACP) methodology used in food manufacturing and meets applicable European Union regulations. Shelf life is enhanced by known technology, such as pasteurization or sterilization. There can be a few possible preparations. One is as a concentrate powder which comprises a step of dilution in water, other is prepared as a bottled ready-to-use liquid. Others can be gel, spray, quick dissolve tablet and other preparations. The important feature is that it will be always a ready to use oral formulation. The oral liquid rehydration formulation of the invention may be bottled in any desired volume size, and different volume sizes are ideally offered since the volume needed for small animals will clearly be quite different from the need of large animals.

Palatability of the oral liquid rehydration formulated according to the invention has also been shown to be high, both in clinical usage and manufacturer's feeding trials. In a two-day palatability trial using 30 dogs, 96% of the dogs preferred the oral liquid rehydration formulation of the invention containing chicken liver hydrolysate and no sodium citrate or citric acid as their first choice compared to a reconstituted powdered product. In this trial, the particular formulation according to the invention which was used was the formulation set out in Example 2 below using the particular flavor enhancer specified in Example 3. The reference product was a prior art product of the following composite which includes citric acid and potassium citrate.

In a particularly preferred arrangement, the protein source can come from a plant source, instead of an animal source. Plants components like cereals (rice, whey or wheat for example) can be used a protein source where the "meat taste" is not required.

Prior Art Formulations

The Pig Site (which is incorporated herein as a reference http://www.thepigsite.com/pighealth/article/103/rehydration-by-mouth) provides the following formula:

| Ingredient | in % |
| --- | --- |
| Glucose | 67.50 |
| Sodium chloride | 14.30 |
| Glycine | 10.40 |
| Potassium dihydrogen phosphate | 6.80 |
| Citric acid | 0.80 |
| Potassium citrate | 0.20 |

DeLaval Pty Ltd (which is incorporated herein as a reference) describes the following rehydration therapy for calf scours:

| Ingredient | in % |
| --- | --- |
| Dextrose | >80.00 |
| Sodium chloride | <10.00 |
| Sodium Bicarbonate | <10.00 |

Patent application WO1997042943A1 (which is incorporated herein as a reference) provides the following formulations:

| Ingredient | in % |
| --- | --- |
| Sodium Citrate Dihydrate | 4.68 |
| Sodium Acetate Trihydrate | 3.91 |
| Sodium Propionate | 2.29 |
| Sodium Chloride | 5.58 |
| Potassium Chloride | 3.55 |
| Potassium Dihydrogen Phosphate | 1.62 |
| Dextrose | 75.23 |
| Sunset Yellow | 0.10 |
| Silicon Dioxide | 3.00 |

| Ingredient | in % |
| --- | --- |
| Sodium Citrate | 5.89 |
| Sodium Acetate | 3.27 |
| Sodium Propionate | 1.15 |
| Sodium Chloride | 2.82 |
| Potassium Chloride | 1.76 |
| Potassium Dihydrogen Phosphate | 1.62 |
| Dextrose | 81.97 |
| Sunset Yellow | 0.06 |
| Silicon Dioxide | 3.01 |

Oral Rehydration Therapy in Gastrointestinal Disease

While it might seem counter-intuitive to administer enteral products to patients who have gastroenteritis, this is exactly what was proven to work in human medicine. Gastroenteritis has many aetiologies in farm animals. Most are viral, though some patients develop gastroenteritis for unknown reasons. Dietary indiscretion is also reasonably common. Parvovirus is a particularly severe form of gastroenteritis in dogs. Cells lining the intestinal tract are directly attacked by parvovirus, causing inflammation, subnormal absorption of nutrients, and hemorrhages. Parvovirus also causes a particularly severe nausea and secretory diarrhea. Many veterinary staff are reluctant to feed patients who are vomiting, especially those with parvovirus. However, in a well-designed study of 30 parvovirus pups less than 24 weeks old, Mohr et al showed a more rapid return of appetite, more rapid weight gain and better intestinal wall integrity in pups who received early enteral nutrition by naso-oesophageal tube compared to those who were fed a low-fat tinned food (Mohr et al., Effect of early enteral nutrition on intestinal permeability, intestinal protein loss, and outcome in dogs with severe parvoviral enteritis. J Vet Intern Med. 2003 November-December; 17(6):791-8.—which is incorporated herein as a reference).

In another well-designed study on piglets, Kansagra et al. showed that the lack of enteral nutrition leads to gut atrophy, specifically mucosal atrophy. The study showed notable decreases in jejunal mass (34.8%), villus height (44.4%), and villus area (56.1%) of non-enteral-fed piglets compared with controls. However, in the ileum, only tissue mass (33.9%), protein, and DNA content were reduced by lack of enteral nutrition, whereas villus height and area were unaffected. These findings are not necessarily novel and highlight the fact that the proximal mucosa is more susceptible to lack of ENT nutrients than the distal gut (Kansagra et al., Total parenteral nutrition adversely affects gut barrier function in neonatal piglets. Am J Physiol Gastrointest Liver Physiol. 2003 December; 285(6):G1162-70—which is incorporated herein as a reference).

A third type of gastrointestinal problem that is common in small animal patients is the post-operative recuperation after gastrointestinal surgery. Again, historically, recommendations were to not feed the patient for at least 24 hours after surgery and sometimes longer. Patients who have recently undergone intestinal surgery are at particular risk of intestinal motility disorders, particularly ileus. However, the presence of food within the intestine actually promotes normal motility and stimulates mucosal perfusion, which speeds healing (Chan D L, Gastrointestinal dysfunction in the critical patient. 2007. British small animal veterinary association, Birmingham England—which is incorporated herein as a reference).

The oral liquid rehydration formulation of the present invention is ideal for treating the above conditions. Due to the presence of a flavoring which is palatable to animals, it is also more likely to be taken voluntarily by the ill animal, and due to the presence of glutamate-based specific amino acids.

Since the oral liquid rehydration formulation of the present invention is produced as concentrate powder and also as pre-mixed, it can easily be used in the farm setting for animals who are unwell, but not ill enough to require care in a clinic. It is equally useful for animals who are recuperating following care in a clinic or even human patients recovering at their homes.

The term 'about' refers hereinafter to a value being 25% lower or greater than the defined measure.

Example 1

Administering Oral Rehydration Therapy

Oral rehydration therapy fluid of the present invention may be initially given at a rate of about 0.5 ml/kg every 2 hours, given orally, using a syringe if necessary. This is a very small volume which rarely precipitates vomiting. If no vomiting occurs, this volume may be increased by 50% every 8-12 hours. For cats and small dogs, ice cube trays can be used to freeze small blocks of the oral liquid rehydration formulation and then dispensed as needed. Once the patient begins to lap the fluid, then volumes can be increased rapidly and more calorie-dense food can be introduced.

Oral rehydration therapy also has a place in outpatient treatment of various other conditions. Oral rehydration therapy, particularly if it is a highly palatable product such as the oral liquid rehydration formulation of the present invention, can be used as part of a dietary management plan for patients with mild gastroenteritis. In many of these patients, a short period of fasting combined with small amounts of fluid intake is sufficient to relieve the symptoms.

Owners and lay staff can easily learn how to administer the oral liquid rehydration formulation of the present invention, as no special skill is required to use it.

Example 2

An example of a hydrolized wheat protein source oral rehydration formulation according to the invention is as follows:

| Ingredient | in % |
| --- | --- |
| Water | 96.27 |
| Glucose monohydrate | 1.50 |
| Sodium chloride | 0.26 |
| Potassium chloride | 0.15 |
| Glycine | 0.40 |
| Trisodiumcitrate | 0.29 |
| Xanthan gum | 0.05 |
| Hydrolysed wheat protein | 1.00 |
| L-glutamic acid | 0.04 |
| Monosodium glutamate | 0.04 |

Concentrate Formulation of Example 2

A concentrate may be prepared as follows:

| Ingredient | in % |
| --- | --- |
| Water | 62.70 |
| Glucose monohydrate | 15.00 |
| Sodium chloride | 2.60 |
| Potassium chloride | 1.50 |
| Glycine | 4.00 |
| Trisodiumcitrate | 2.90 |
| Xanthan gum | 0.50 |
| Hydrolysed wheat protein | 10.00 |
| L-glutamic acid | 0.40 |
| Monosodium glutamate | 0.40 |

The concentrate is mixed and held at room temperature for at least 5 minutes. Typical pH is about 3.7 to 3.8 at 20° C. after 10× dilution, for use. To dilute for use, 10 ml of concentrate is added into 90 ml water and mixed.

Example 3

Oral Liquid Rehydration Formulation for Pigs, Calves and Lambs

An example of a hydrolized wheat protein source oral rehydration formulation according to the invention is as follows:

| Ingredient | in % |
| --- | --- |
| Water | 96.26 |
| Glucose monohydrate | 1.50 |
| Sodium chloride | 0.26 |
| Potassium chloride | 0.15 |
| Glycine | 0.40 |
| Sodium dihydrogen phosphate | 0.10 |
| Xanthan gum | 0.05 |
| Hydrolysed wheat protein | 1.00 |
| L-glutamic acid | 0.04 |
| Monosodium glutamate | 0.04 |

Concentrate Formulation of Example 3

A concentrate may be prepared as follows:

| Ingredient | in % |
| --- | --- |
| Water | 62.60 |
| Glucose monohydrate | 15.00 |
| Sodium chloride | 2.60 |
| Potassium chloride | 1.50 |
| Glycine | 4.00 |
| Sodium dihydrogen phosphate | 1.00 |
| Xanthan gum | 0.50 |
| Hydrolysed wheat protein | 10.00 |
| L-glutamic acid | 0.40 |
| Monosodium glutamate | 0.40 |

The concentrate is mixed and held at room temperature for at least 5 minutes. Typical pH is about 3.7 to 3.8 at 20° C. after 10× dilution, for use. To dilute for use, 10 ml of concentrate is added into 90 ml water and mixed.

Example 4

Oral Liquid Rehydration Formulation for Pigs, Calves and Lambs

An example of a hydrolized wheat protein source oral rehydration formulation according to the invention is as follows:

| Ingredient | in % |
| --- | --- |
| Water | 97.00 |
| Glucose monohydrate | 1.45 |
| Sodium chloride | 0.26 |
| Potassium chloride | 0.15 |
| Glycine | 0.30 |
| Sodium dihydrogen phosphate | 0.10 |
| Xanthan gum | 0.10 |
| Citric Acid Monohydrate | 0.20 |
| Hydrolysed whey protein | 0.15 |
| L-glutamic acid | 0.04 |
| Monosodium glutamate | 0.25 |
| 85% Steviol Glycoside extract | 0.001 |

Powder Formulation of Example 4

A powder may be prepared as follows:

| Ingredient | in % |
| --- | --- |
| Water | 97.00 |
| Glucose monohydrate | 48.33 |
| Sodium chloride | 8.67 |
| Potassium chloride | 5.00 |
| Glycine | 10.00 |
| Sodium dihydrogen phosphate | 3.33 |
| Xanthan gum | 3.33 |
| Citric Acid Monohydrate | 6.67 |
| Hydrolysed whey protein | 5.00 |
| L-glutamic acid | 1.33 |

| Ingredient | in % |
| --- | --- |
| Monosodium glutamate | 8.30 |
| 85% Steviol Glycoside extract | 0.033 |

The powder is mixed and held at room temperature for at least 5 minutes. Typical pH is about 3.8 to 4.0 at 20° C. after dilution of 3.0 parts of powder with 97.0 parts of water. To dilute for use, 468 gr. of powder in 4 US gallons (15.14 liters) of water and mixed.

Example 5

Oral Liquid Rehydration Formulation for Pigs, Calves and Lambs

Another example of a hydrolized whey protein source oral rehydration formulation according to the invention is as follows:

| Ingredient | in % |
| --- | --- |
| Water | 97.00 |
| Glucose monohydrate | 1.44 |
| Sodium chloride | 0.26 |
| Potassium chloride | 0.15 |
| Glycine | 0.30 |
| Sodium dihydrogen phosphate | 0.10 |
| Xanthan gum | 0.10 |
| Citric Acid Monohydrate | 0.20 |
| Hydrolysed whey protein | 0.15 |
| L-glutamic acid | 0.04 |
| Monosodium glutamate | 0.25 |
| 85% Steviol Glycoside extract | 0.01 |

Powder Formulation of Example 5

A powder may be prepared as follows:

| Ingredient | in % |
| --- | --- |
| Water | 97.00 |
| Glucose monohydrate | 48.03 |
| Sodium chloride | 8.67 |
| Potassium chloride | 5.00 |
| Glycine | 10.00 |
| Sodium dihydrogen phosphate | 3.33 |
| Xanthan gum | 3.33 |
| Citric Acid Monohydrate | 6.67 |
| Hydrolysed whey protein | 5.00 |
| L-glutamic acid | 1.33 |
| Monosodium glutamate | 8.30 |
| 85% Steviol Glycoside extract | 0.33 |

The powder is mixed and held at room temperature for at least 5 minutes. Typical pH is about 3.8 to 4.0 at 20° C. after dilution of 3.0 parts of powder with 97.0 parts of water. To dilute for use, 468 gr. of powder in 4 US gallons (15.14 liters) of water and mixed.

Oral rehydration therapy has an important place in the management of veterinary patients. The oral liquid rehydration formulation of the present invention may be used as an initial supportive treatment in any anorexic or vomiting animal and can be used alongside intravenous fluids. Oral rehydration therapy may be continued until a transition to more complex foods can be made. Oral rehydration therapy using the oral liquid rehydration formulation of the present invention allows the body to gain essential nutrients and electrolytes without burdening digestive processes. Oral liquid rehydration formulation according to this invention which are highly palatable and which are nutritious to veterinary patients are likely to be better accepted and tolerated.

It is to be understood that the invention is not limited to the specific detail described above which are given by way of example only and that various modifications and alterations are possible without departing from the scope of the invention.

What is claimed is:

1. An isotonic oral rehydration composition comprising:
    (a) glutamic acid in a range of about 0.01% to about 0.40% w/w;
    (b) about 1.50% w/w glucose monohydrate;
    (c) about 0.20% w/w sodium chloride;
    (d) about 0.15% w/w potassium chloride;
    (e) about 0.15% w/w sodium dihydrogen phosphate;
    (f) about 0.10% w/w xanthan gum;
    (g) hydrolyzed whey in a range of about 0.15% to about 1.00% w/w;
    (h) about 0.20% w/w citric acid monohydrate;
    (i) 85% Steviol Glycoside extract in a range of about 0.01% to about 0.03% w/w;
    (j) monosodium glutamate in a range of about 0.05% to about 0.80% w/w; and
    (k) about 0.35% w/w glycine.

2. The oral rehydration composition of claim 1, wherein said composition further comprises:
    (l) about 0.30% w/w trisodium citrate; and
    (m) about 1.00% w/w hydrolyzed wheat.

3. The oral rehydration composition of claim 1, wherein said composition is tailored to suit the flavouring preferences of different species or individuals.

4. The oral rehydration composition of claim 1, wherein said composition is a ready-to-use composition.

5. The oral rehydration composition of claim 1, wherein said composition is a powder concentrate.

6. The oral rehydration composition of claim 5, wherein said concentrate is diluted in water.

7. The oral rehydration composition of claim 5, wherein said concentrate comprises enzyme co-factors.

8. The oral rehydration composition of claim 1, wherein said composition is an isotonic solution.

9. The oral rehydration composition of claim 8, wherein said isotonic solution is comparable to the isotonicity of a 0.9% solution of sodium chloride.

10. The oral rehydration composition of claim 1, wherein said composition can be a gel, a spray or a quick dissolve tablet.

11. A method of treating dehydration in an individual comprising:
    (i) preparing an isotonic oral rehydration solution comprising:
        (a) glutamic acid in a range of about 0.01% to about 0.40% w/w;
        (b) about 1.50% w/w glucose monohydrate;
        (c) about 0.20% w/w sodium chloride;
        (d) about 0.15% w/w potassium chloride;
        (e) about 0.15% w/w sodium dihydrogen phosphate;
        (f) about 0.10% w/w xanthan gum;
        (g) hydrolyzed whey in a range of about 0.15% to about 1.00% w/w;
        (h) about 0.20% w/w citric acid monohydrate;
        (i) 85% Steviol Glycoside extract in a range of about 0.01% to about 0.03% w/w;

(j) monosodium glutamate in a range of about 0.05% to about 0.80% w/w; and
(k) about 0.35% w/w glycine, and
(ii) administering said isotonic oral rehydration solution to the individual.

12. The method of claim 11, wherein said individual is an animal.

13. The method of claim 11, wherein said individual is an animal.

14. The method of claim 11, wherein said individual is suffering from diarrhea.

* * * * *